US009351951B2

(12) United States Patent
Xue et al.

(10) Patent No.: US 9,351,951 B2
(45) Date of Patent: May 31, 2016

(54) PREVENTION OF PROTEOMIC AND GENOMIC DAMAGE BY DICARBONYL SUBSTRATES OF GLO 1

(75) Inventors: Mingzhan Xue, Coventry (GB); Paul Thornalley, Coventry (GB); Naila Rabbani, Coventry (GB)

(73) Assignee: University of Warnick, Coventry (GB)

( * ) Notice: Subject to any disclaimer, the term of this patent is extended or adjusted under 35 U.S.C. 154(b) by 682 days.

(21) Appl. No.: 13/806,176

(22) PCT Filed: Jun. 20, 2011

(86) PCT No.: PCT/GB2011/051143
§ 371 (c)(1),
(2), (4) Date: May 8, 2013

(87) PCT Pub. No.: WO2011/161436
PCT Pub. Date: Dec. 29, 2011

(65) Prior Publication Data
US 2013/0231387 A1    Sep. 5, 2013

(30) Foreign Application Priority Data

Jun. 22, 2010  (GB) .................................. 1010418.0

(51) Int. Cl.
| C12Q 1/68 | (2006.01) |
| C12N 15/63 | (2006.01) |
| A61K 31/26 | (2006.01) |
| C12N 9/88 | (2006.01) |
| C12Q 1/25 | (2006.01) |
| A61K 45/06 | (2006.01) |
| C07C 331/20 | (2006.01) |
| C07C 331/22 | (2006.01) |

(52) U.S. Cl.
CPC ................ *A61K 31/26* (2013.01); *A61K 45/06* (2013.01); *C07C 331/20* (2013.01); *C07C 331/22* (2013.01); *C12N 9/88* (2013.01); *C12Q 1/25* (2013.01); *G01N 2500/00* (2013.01); *G01N 2570/00* (2013.01)

(58) Field of Classification Search
None
See application file for complete search history.

(56) References Cited

U.S. PATENT DOCUMENTS 5,248,504 A * 9/1993 Friedman ...................... 424/434
8,367,342 B2 * 2/2013 Da Costa Martins
                         et al. ............................. 435/6.13

OTHER PUBLICATIONS

Ranganathan et al., Gene v. 240 (1999) pp. 149-155.*
International Search report and Written Opinion for International application No. PCT/GB2011/051146 dated Dec. 23, 2011.

M. Xue et al.; "Activation of NF-E2-Related Factor-2 Reverses Biochemical Dysfunction of Endothelial Cells Induced by Hyperglycemia Linked to Vascular Disease"; Diabetes, vol. 57, Oct. 2008, pp. 2809-2817.
S. Ranganathan, et al.; "Genomic sequence of human glyoxalase-I: analysis of promoter activity and its regulation"; Elsevier Science B.V., 1999; Gene, vol. 240, No. 1, pp. 149-155.
T. Hsieh, et al.; "Induction of quinone reductase NQ01 by reservatrol involves antioxidant response element ARE and is accompanied by nuclear translocation of transcription factor Nrf2"; FASEB Journal, Apr. 5, 2006, Fed. of American Soc. for Experimental Biology, vol. 20, No. 4, Part 1, p. A82.
M. Morcos, et al.; "Life extension in Caenorhabditis elegans by over expression of Glyoxalase I—A mechanistic integration of protein damage by glycation, oxidation and nitratio"; Molecular and Integrative Physiology, Elsevier Science, New York, NY; Comparative Biochemistry and Physiology, Part A, vol. 146, No. 4, Apr. 1, 2007, p. S59.
P.J. Thornalley; "Protecting the genome: defence against nucleotide glycation and emerging role of glyoxalase I overexpression in multidrug resistance in cancer chemotherapy"; Portland Press Ltd, GB; Biochemical Society Transactions (2003), vol. 31, Part 6, pp. 1372-1377.
E. Abordo, et al.; "Accumulation of a-Oxoaldehydes during Oxidative Stress: A Role in Cytotoxicity"; Biochemical Pharmacology, 1999, vol. 58, pp. 641-648.
B. Duran-Jimenez, et al.; "Advanced Glycation End Products in Extracellular Matrix Proteins Contribute to the Failure of Sensory Nerve Regeneration in Diabetes"; Diabetes, vol. 58, Dec. 2009, pp. 2893-2903.
W. Wasserman, et al.; "Functional antioxidant responsive elements"; Proc. Natl. Acad. Sci. USA, vol. 94, May 1997, pp. 5361-5366, Medical Sciences.
N. Rabbani, et al.; "Glycation of LDL by Methylglyoxal Increases Arterial Atherogenicity; A possible Contributor to Increased Risk of Cardiovascular Disease in Diabetes"; Diabetes; published online May 26, 2011 at diabetes. diabetesjournals.org; pp. 1-8.
T. Kumagai, et al.; "Glyoxalase I overexpression ameliorates renal ischemia-reperfusion injury in rats"; American Journal of Physiology Renal Physiology, vol. 296, pp. F912-F921, 2009.
M. Morcos, et al.; "Glyoxalase-1 prevents mitochondrial protein modification and enhances lifespan in Caenorhabditis elegans"; Aging Cell, 2008, vol. 7, pp. 260-269.
P.J. Thornalley; "Glyoxalase I—structure, function and a critical role in the enzymatic defence against glycation"; Biochemical Society Transactions (2003), vol. 31, part 6, pp. 1343-1348.
N. Rabbani, et al.; Glyoxalase in diabetes, obesity and related disorders; Seminars in Cell & Development Biology (2011), vol. 22, pp. 309-317.
D. Yao, et al.; "High Glucose Increases Angiopoietin-2 transcription in Microvascular Endothelial Cells through Methylglyoxal Modification of mSin3A"; Journal of Biological Chemistry, Oct. 19, 2007, vol. 282, No. 42; pp. 31038-31045.

(Continued)

*Primary Examiner* — Jim Ketter
(74) *Attorney, Agent, or Firm* — King & Schickli, PLLC

(57) ABSTRACT

The invention concerns the role of Glo 1 in the prevention and reversal of proteomic and genomic damage by carbonyl substrates thereof and, in particular, therapeutics that promote Glo 1 production.

22 Claims, 7 Drawing Sheets

(56) References Cited

OTHER PUBLICATIONS

Figure 1:
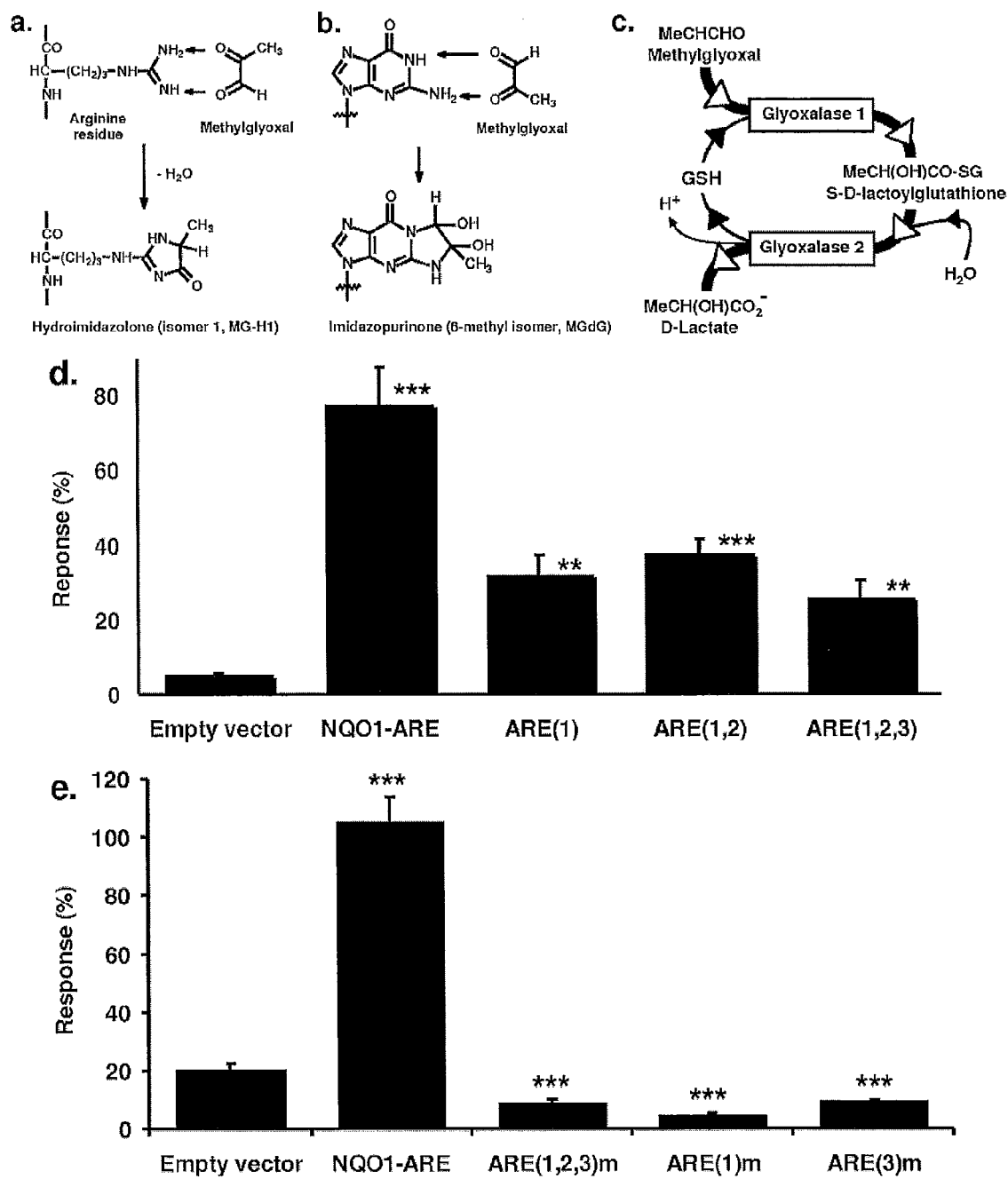

P. Thornalley, et al.; "Highlights and Hotspots of Protein Glycation in End-Stage Renal Disease"; Progress in Uremic Toxin Research, Seminars in Dialysis (2009), vol. 22, No. 4, pp. 400-404.

O. Brouwers, et al.; "Hyperglycaemia-induced impairment of endothelium-dependent vasorelaxation in rat mesenteric arteries is mediated by intracellular methylglyoxal levels in a pathway dependent on oxidative stress"; Diabetologia (2010), vol. 53, pp. 989-1000.

X. Wang, et al.; "Identification of polymorphic antioxidant response elements (AREs) in the human genome"; Hum Mol Genet., 2007, vol. 16(10), pp. 1188-1200.

D. Dobler, et al.; "Increased Dicarbonyl Metabolism in Endothelial Cells in Hyperglycemia Induces Anoikis and Impairs Angiogenesis by RGD and GFOGER Motif Modification"; Diabetes, vol. 55, Jul. 2006, pp. 1961-1969.

S.B. Stoyanov, et al.; "Loss of glyoxalase-1 promotes hyperalgesia in early diabetic neuropathy"; Diabetologia (2009), vol. 52 (Suppl. 1), 1146, pp. S444-S445.

C. Gasche, et al.; "Oxidative Stress Increases Farmeshift Mutations in Human Colorectal Cancer Cells"; Cancer Research, Oct. 15, 2001, vol. 61, pp. 7444-7448.

P.J. Thornalley; "Protein and nucleotide damage by glyoxal and methylglyoxal in physiological systems—role in ageing and disease"; Drug Metabol Drug Interact, 2008, vol. 23(1-2), pp. 125-150.

U. Ahmed, et al.; "Reversal of Hyperglycemia-Induced Angiogenesis Deficit of Human Endothelial Cells by Overexpression of Glyoxalase 1 In Vitro"; Ann. New York Academy of Sciences, vol. 1126, pp. 262-264 (2008).

I. Konrade, et al.; RAGE-dependent impairment of glyoxalase-1 contributes to functional deficits in diabetic neuropathy; Diabetologia (2006), vol. 49 (Suppl. 1), p. 662.

P.J. Thornalley; "The Glyoxalase System in Health and Disease"; Molec. Aspects Med., vol. 14, pp. 287-371, 1993.

P.J. Thornalley; "The Potential Role of Thiamine (Vitamin B1) in Diabetic Complications"; Current Diabetes Reviews, 2005, vol. 1, No. 3, pp. 287-298.

M. Xue, et al.; "Glyoxalase in ageing"; Seminars in Cell & Development Biology, vol. 22, pp. 293-301, 2011.

* cited by examiner

PREVENTION OF PROTEOMIC AND GENOMIC DAMAGE BY DICARBONYL SUBSTRATES OF GLO 1

This application is the national stage of international patent application no. PCT/GB2011/051143 filed on Jun. 20, 2011, which in turn claims priority from British Patent Application Ser. No. GB1010418.0 filed on Jun. 22, 2010, the disclosures of each of which are incorporated herein by reference in their entirety.

The invention relates to a screening method and kit, including parts thereof, for detecting agents or therapeutics useful in preventing damage to the mammalian proteome or genome; agents or therapeutics identified thereby; pharmaceutical compositions including said agents or therapeutics; use of said agents, therapeutics or compositions in the treatment of a range of disorders; novel promoters for the GLO1 gene; novel constructs for use in said, method; and cells or cell lines when transformed or transfected with said constructs. The invention has application in the medical and veterinary fields.

INTRODUCTION

Formation of a dicarbonyl metabolite, methylglyoxal (MG), is unavoidable in glycolytic organisms by the trace degradation of triosephosphate intermediates. MG is a potent glycating agent. It mainly modifies arginine residues of proteins to form a hydroimidazolone (MG-H1) with other adduct formation, usually minor, on lysine (Nε-(1-carboxyethyl) lysine CEL and lysine dimer, 4-methylimidazolium MOLD) and arginine residues (argpyrimidine). It mainly modifies deoxyguanosine residues of DNA to form a imidazopurinone (MGdG) with other, usually minor, adduct formation ($N_2$-(1-carboxyethyl)deoxyguanosine CEdG)—please see FIGS. 1a and 1b. Protein modification by MG is often directed to functional sites and it is associated with a profound decrease in binding interactions and loss of function such as detachment of endothelial cells by loss of integrin binding to type IV collagen, dysfunction of mitochondrial proteins and increasing the formation of reactive oxygen species. Modification of DNA is associated with DNA strand breaks and mutations at chromosomal hotspots—including frameshift mutations.

It is known that protein and DNA damage by MG is suppressed by Glo1 which catalyses the glutathione (GSH)-dependent conversion of MG to S-D-lactoylglutathione; glyoxalase 2, a thiolesterase, hydrolyses this to D-lactate and reforms GSH consumed in the Glo1-catalysed reaction—please see FIG. 1c. The high reactivity of MG leads to some escape from detoxification such that 1-5% of proteins have an MG-H1 modification and MGdG is one of the DNA damage adducts of highest steady state content in DNA in vivo (ca. 1-10 adducts per $10^6$ nucleotides).

There is increasing evidence from research findings of our group and others of increased protein modification by MG hi the progression of vascular complications of diabetes, renal failure, critical illness, cardiovascular disease, neurological and certain mood affective disorders and ageing. In some cases there has been recent evidence 45 that this may be linked to both increased formation of MG and down regulation of Glo1 expression—the later linked to pro-inflammatory cell signalling. Inflammatory cell signalling, initiated by inflammatory mediators such as tumour-necrosis factor-α, S100A12 protein and others, activates the transcriptional system, nuclear factor kappa-light-chain-enhancer of activated B cells (NF-κB). Counter or conflicting signalling of this system with the transcriptional regulation of Glo expression decreases Glo1 activity leading to increased MG and protein damage. A recent example has been the marked increase of the MG protein, MG-H1, in synovial fluid of patients with rheumatoid arthritis and osteoarthritis[46].

A decrease in MG concentrations in tissues may offer a potential new route for therapeutic intervention in several degenerative and inflammatory diseases and ageing. Unfortunately, though, attempts at therapeutic intervention by the use of methylglyoxal scavengers has been unsuccessful because of toxicity and instability issues. More recent interventions to prevent increased MG formation in diabetes by activating the reductive pentosephosphate pathway using high dose thiamine has proven successful in pilot trials for reversal of early-stage diabetic nephropathy. However, this may have limited applicability i.e. for correcting increased washout of thiamine in diabetes. Hyperglycaemia associated with diabetes induces a down regulation of thiamine transporters in the renal tubular epithelium leading to decreased reuptake of thiamine from the glomerular filtrate, increased renal clearance of thiamine and thiamine deficiency limited to the kidney and other tissues damaged by chronic hyperglycaemia (retina and peripheral nerve). This produces a related tissue-specific deficiency in the thiamine pyrophosphate-dependent enzyme transketolase (TK), related accumulation of triosephosphate glycolytic intermediate and increased formation of MG. High dose thiamine supplementation re-establishes TK activity, diverts excess triosephosphates to pentosephosphate synthesis and prevents increased MG formation. This and other dysfunctional metabolism reversed by thiamine in diabetes is linked to prevention and reversal of early-stage nephropathy in diabetes[47].

We have therefore set about, identifying a therapeutic intervention of widespread application that overcomes the above toxicity and stability issues and, moreover, has widespread application.

STATEMENTS OF INVENTION

According to a first aspect of the invention there is provided a screening method for identifying agents that prevent and/or reverse proteomic and/or genomic damage produced by dicarbonyl substrates of Glo1 by inducing the increased expression of the GLO1 gene comprising:

a) providing a cell including the GLO1 gene and its associated transcription machinery for producing a Glo1 gene product;
b) exposing said cell to at least one test agent;
c) investigating said cell for the production of said Glo1 gene product; and
d) where said product is produced, or its amount increased, after exposure to the test agent, concluding said test agent has use in inducing the expression of GLO1 and so preventing proteomic and genomic damage produced by dicarbonyl substrates of Glo1.

Thus we have, discovered that the optimum and generally applicable therapeutic intervention for the prevention and/or reversal of glycation of the proteome and/or genome produced by dicarbonyl substrates of Glo1 is achieved by inducing increased expression of GLO1.

Notably, reversal is possible because formation of the protein adduce MG-H1 has slow dynamic reversibility (half-life 12 days) and the DNA adduct faster dynamic reversibility (half-life 12 h) such that a decrease of MG concentration will produce some reversal—particularly for DNA and long-lived proteins.

In a preferred embodiment of the invention said cell is a recombinant cell that has been transformed or transfected with a construct encoding said GLO1 gene and, ideally, its associated transcription machinery. In the instance where said construct only encodes GLO1 said cell is provided with the necessary machinery to enable the production of Glo1.

In a further preferred embodiment of the invention step c) above involves a conventional assay such as the one described herein for measuring Glo1 gene product using a reporter assay. Additionally, or alternatively step c) above may involve assaying for the activity of Glo1 using a conventional assay such as the one described herein involving determining the initial rate of isomerisation of the hemithioacetal formed from methylglyoxal and GSH to S-D-lactoylglutathione followed spectrophotometrically at 240 am. Alternatively the Glo1 gene product can be measured by Western blotting or any other conventional protein assays such as, for example, antibody binding assays.

Further we have also realised that multiple health benefits may be accrued from increased expression and/or activity of Glo1. Our investigations have lead us to conclude that in pathogenetic mechanisms, overexpression of Glo1 prevented: (i) dysfunction of compressor mSin3A in renal endothelial cells leading to increased angiopoietin-2 and pro-inflammatory signalling in progression of nephropathy.[13] (ii) dysfunction of hypoxia-inducible factor-1α leading to impaired endothelial progenitor cell and endoethial nitric oxide synthase response and failure to correct tissue hypoxia,[14] (iii) sustained release of p65 and prolonged activation of the NF-κB system amplifying inflammation,[15] and (iv) impairment of the proteasome system. In vascular systems, overexpression of Glo1 prevented impairment of angiogenesis in hyperglycaemia,[17] impairment of NO-mediated vascular dilatation in diabetes[18] and renal ischemia-reperfusion injury.[19] In whole organism health, overexpression of Glo1 in *Caenorhabditis elegans* produced increased in median and maximum lifespan.[20]

Our research has led us to discover that Glo1 expression is under the control of a known antistress gene response coordinated by nuclear factor erythroid 2-related factor 2 (nrf2) which binds to antioxidant response elements (AREs)[21] in a gene promoter. We have, identified a number of these binding domains i.e. antioxidant response elements (AREs) in the Glo1 gene promoter.

Accordingly, in a preferred embodiment said cell or construct comprises said GLO1 gene including its associated wild-type promoter region wherein said region comprises a plurality of AREs. Alternatively, or additionally, said cell or construct comprises said Glo1 gene, and an artificial promoter region comprising at least one, and preferably a plurality of, AREs.

Most preferably said promoter region comprises an ARE defined by the following sequence structure 5'-GTGATACTGCA-3' (ARE1) (SEQ ID NO: 1).

Most preferably still said promoter region comprises an ARE defined by the following sequence structure 5'-ATGAGTTTGCC-3' (ARE2) (SEQ ID NO: 2).

Most preferably said promoter region comprises an ARE defined by the following sequence structure 5'-ATGACTAAGCC-3' (ARE3) (SEQ ID NO: 3).

Yet more preferably, said promoter region comprises at least one copy of ARE1, and/or ARE2 and/or ARE3 i.e. sequences 5'-GTGATACTGCA-3' (SEQ ID NO: 1) and 5'-ATGAGTTTGCC-3' (SEQ ID NO: 2) and 5'-ATGACTAAGCC-3' (SEQ ID NO: 3).

Yet more preferably still, said promoter region comprises at least one copy and, ideally, multiple copies of ARE1.

Reference herein to ARE1 is reference to antioxidant response element located at (numbered from the start codon): −10 to −19, sequence 5'-GTGATACTGCA-3' (SEQ ID NO: 1) in exon-1 of GLO1.

Reference herein to ARE2 is reference to antioxidant response element located at (numbered, from the start codon): −261 to −252, sequence 5' (SEQ ID NO: 2) in the promoter of GEO 1.

Reference herein to ARE3 is reference to antioxidant response element located at (numbered from the start codon): −1060 to −1051, sequence 5'-ATGACTAAGCC-3' SEQ ID NO: 3) in the promoter of GLO1.

In a preferred, embodiment said construct is an ARE positive reporter vector, such as, pGL3-NQO1ARE. Ideally, the insertion sequence of said construct is as follows: (ARE motif is underlined and low case letters are the Kpn1 and Nhe1 restriction sites) ggtaccCTCAGCCTTCCAAATCCGCAGT-CACAGTGACTCAGCAGAATCgctagc (SEQ ID NO: 4).

According to a further aspect of the invention there is provided a construct encoding the promoter region of the GLO1 gene functionally linked to the coding region of the GLO1 gene and/or the coding region of a gene encoding a reporter molecule whereby the production of Glo1 product and/or the product of the reporter gene can be monitored.

In a preferred construct said reporter molecule is a fluorescent molecule.

According to a further aspect of the invention there is provided a cell or cell line transformed or transfected with a construct according to the invention.

In a further aspect, the invention comprises the use of a cell or cell line described herein for the identification of agents that induce, the expression of a gene functionally linked to either the wild-type GLO1 promoter or a recombinant version thereof, including an artificial promoter comprising a least one, or a plurality, of the AREs described herein. Ideally said gene is GLO1 or a selected reporter gene.

It will be apparent to those skilled in the art that a knowledge of the promoter region of the GLO1 gene enables us to identify agents useful at inducing GLO1 expression by identifying agents that activate this promoter or a structurally or functionally similar promoter that includes the AREs, including multiple copies thereof, described herein.

According to a further aspect said invention comprises a kit for performing any of the above methods comprising a cell or construct as above described and an assay means for measuring the presence or amount of Glo1 product or the presence or amount, of reporter molecule, or for measuring the activity of Glo1.

According to a further aspect of the invention there is provided a therapeutic for treating or preventing MG glycation of the mammalian proteome and/or genome comprising one or more agent(s) identified by the above method.

Preferably, said therapeutic comprises a nrf2 activator, and more preferably still a natural consumable product such as an isothiocyanate. More preferably said isothiocyanate is sulforaphane (SFN). R- or S-, or both isomers, and/or an allyl isothiocyanate (AITC). More preferably still said therapeutic is formulated so that it is used in the low μM range (rarely above 10 μM, ideally no more than 5-10 μM and usually at 2 or 1 μM or even less) to provide an effective response.

In a preferred embodiment said therapeutic is used to treat any one or more of the following disorders: inflammatory disorders (low-grade and severe), tissue hypoxia, vascular disease, diabetes and its associated complications, renal failure, cardiovascular disease, painful neuropathy, neurological and certain mood affective disorders, ageing, obesity, atherosclerosis, hypertension, pre-diabetes (impaired glucose tolerance) and reproductive, disorders such as hypertension e.g. in preeclampsia and other preterm labour conditions.

According to a further aspect of the invention there is provided a combination therapeutic comprising at least one agent identified by the above method in combination with at least one further selected therapeutic; or a number of agents identified by the above method in combination with at least one further selected therapeutic.

According to a further aspect of the invention there is provided a pharmaceutical composition comprising one or more therapeutics herein described in combination with a medicinal or veterinary carrier.

According to a further aspect of the invention there is provided the use of an agent identified by the above method for treating any one or more, of the following diseases or conditions: inflammatory disorders (low-grade and severe), tissue hypoxia, vascular disease, diabetes and its associated complications, renal failure, cardiovascular disease, painful neuropathy, neurological and certain mood affective disorders, ageing, obesity, atherosclerosis, hypertension, pre-diabetes (impaired glucose tolerance) and reproductive disorders such as hypertension e.g. in preeclampsia and other preterm labour conditions.

According to a further aspect of the invention there is provided a screening method for identifying agents that prevent and/or reverse proteomic and genomic damage produced by dicarbonyl substrates of Glo1 by inducing the increased activity of Glo1 protein comprising:
a) providing a cell or media including the Glo1 protein;
b) exposing said protein to at least one test agent;
c) investigating said protein to determine its activity; and
d) where said activity is increased following exposure to said test agent, concluding said test agent has use in increasing the activity of Glo1 protein and so preventing proteomic and genomic damage produced by dicarbonyl substrates of Glo1.

In a preferred method, step c) above involves assaying for the activity of Glo1 using a conventional assay such as the one described herein involving determining the initial rate of isomerisation of the hemithioacetal formed from methylglyoxal and GSH to S-D-lactoylglutathione followed spectrophotometrically at 240 nm. Alternatively, the Glo1 gene product can be measured by Western blotting or any other conventional protein assays such as, for example, antibody binding assays.

The invention will now be described, by way of example only, with reference to the following figures and tables wherein:—

FIG. 1. Shows major glycation reactions of methylglyoxal, prevention by the glyoxalase system and GLO1 as an ARE-linked gene. a. Formation of hydroimidazolone MG-H1 residues in proteins; b. formation of imidazopurinone MGdG residues in DNA. c. The glyoxalase system. d. Reporter response for GLO1 serial deletion fragments and ARE-NQO1 (positive control), e. Reporter response for GLO1 serial deletion mutant fragments and ARE-NQO1 (positive control). Data are mean±SD (n=3).

Figure 2A:
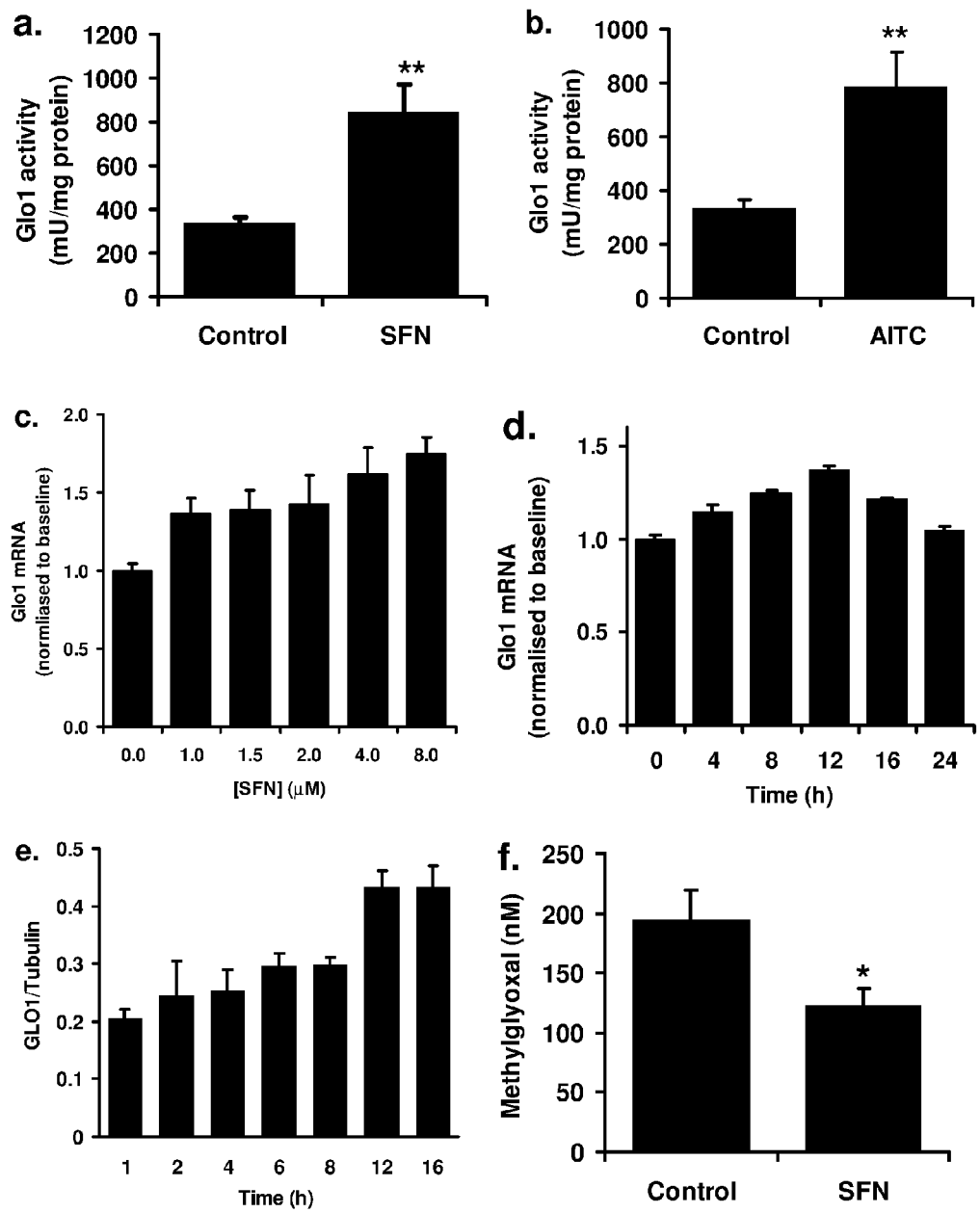

FIG. 2A. Shows induction of glyoxalase 1 expression by sulforaphane and allyl isothiocyanate in human HepG2 cells and BJ fibroblasts in vitro. Induction of Glo1 activity in HepG2 cells in vitro by 2 μM SFN (a.) and 2 μM AITC (b.). HepG2 cells were incubated with inducer for 24 h (c.-j.). Induction of Glo1 expression in BJ fibroblasts in vitro: mRNA dose response (c.) and time course with 2 μM SFN (d.); and time course of Glo1 protein content with 2 μM SFN (e.). Decrease of MG concentration by induction of Glo1 expression in HepG2 cells: concentration of MG in culture medium (f.). Data are mean±SD (n=3).

Figure 2B:
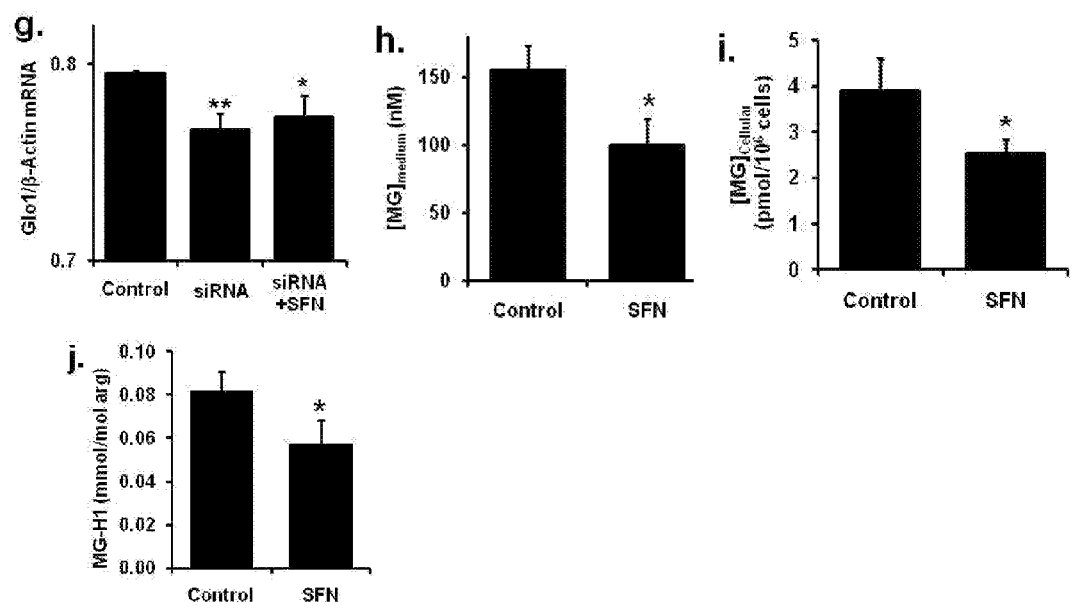

FIG. 2B. Shows induction of glyoxalase 1 expression by sulforaphane and allyl isothiocyanate in human HepG2 cells and BJ fibroblasts in vitro. Effect of nrf2 siRNA on Glo1 mRNA with and without 2 μM SFN (g.); MG concentration in BJ fibroblast cultures—culture medium (h.) and BJ cells (i.) incubated with 2 μM SFN for 48 h (j.). Data are mean ±SD (n=3). Significance: *, P<0.05; , P<0.01; and *, P<0.001 (t-test).

Figure 3:
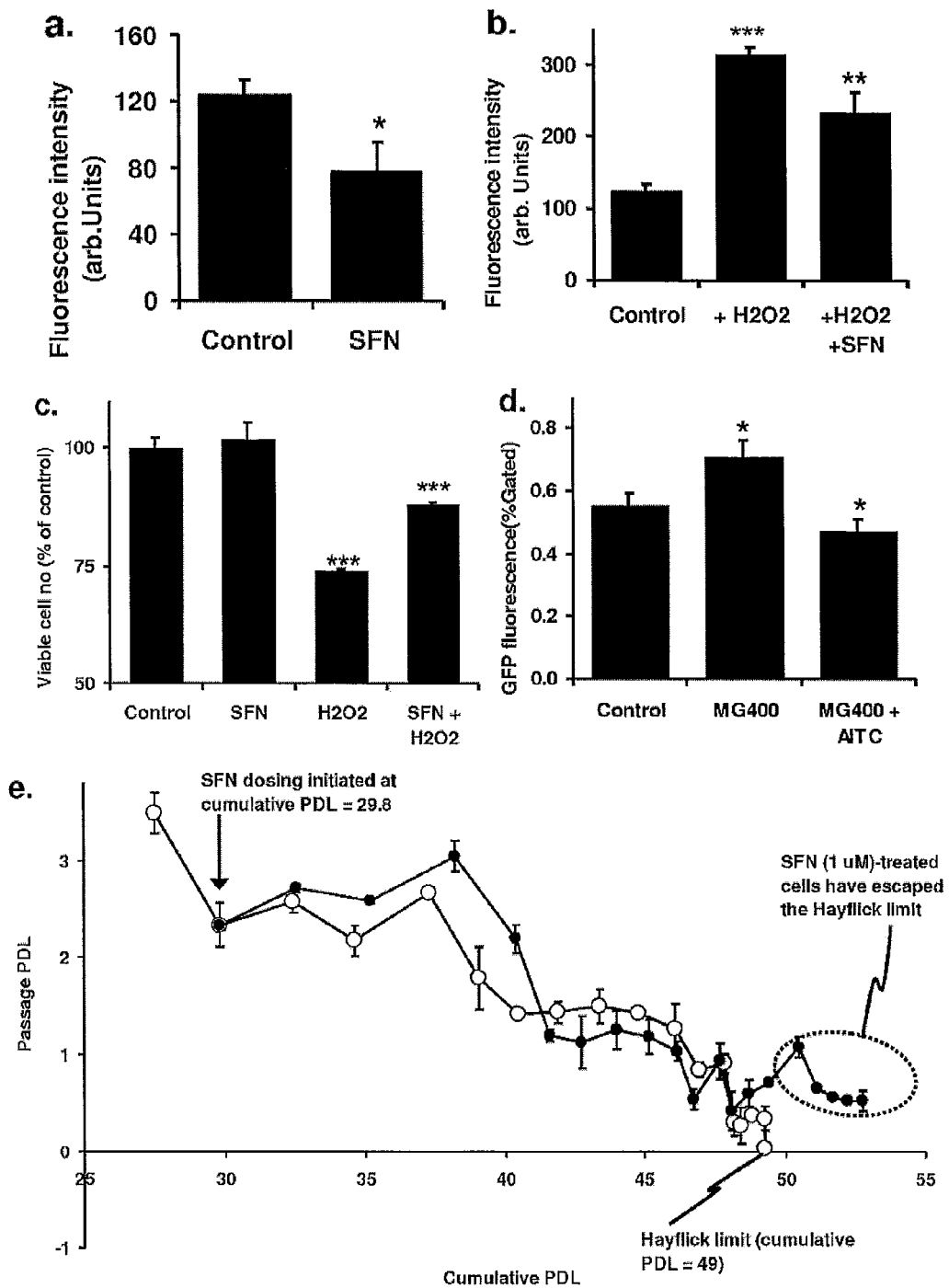
Figure 3:
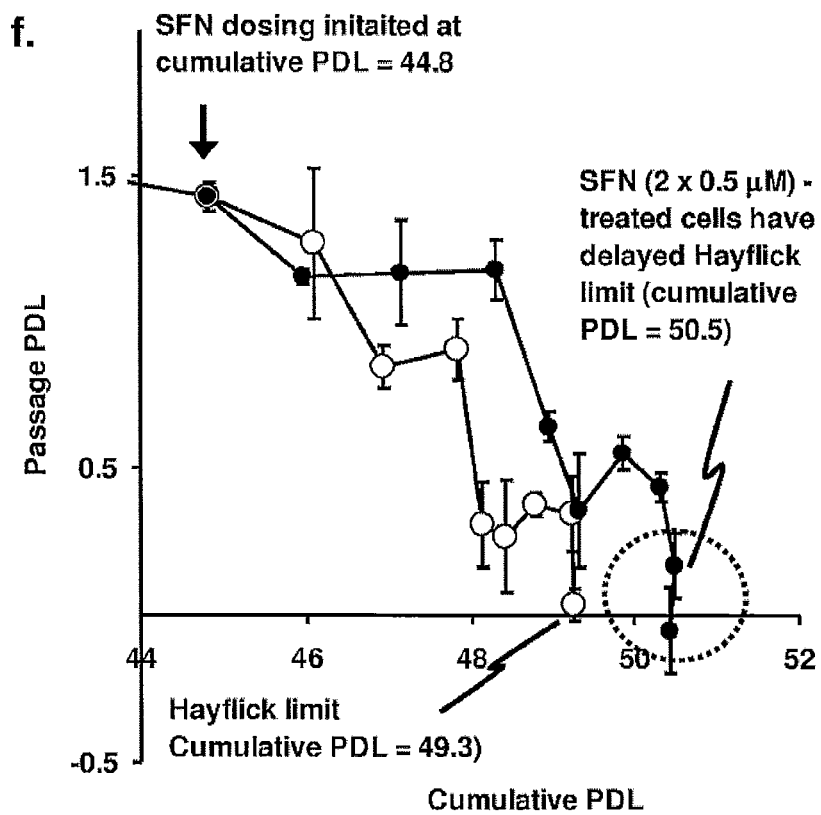
Figure 3:
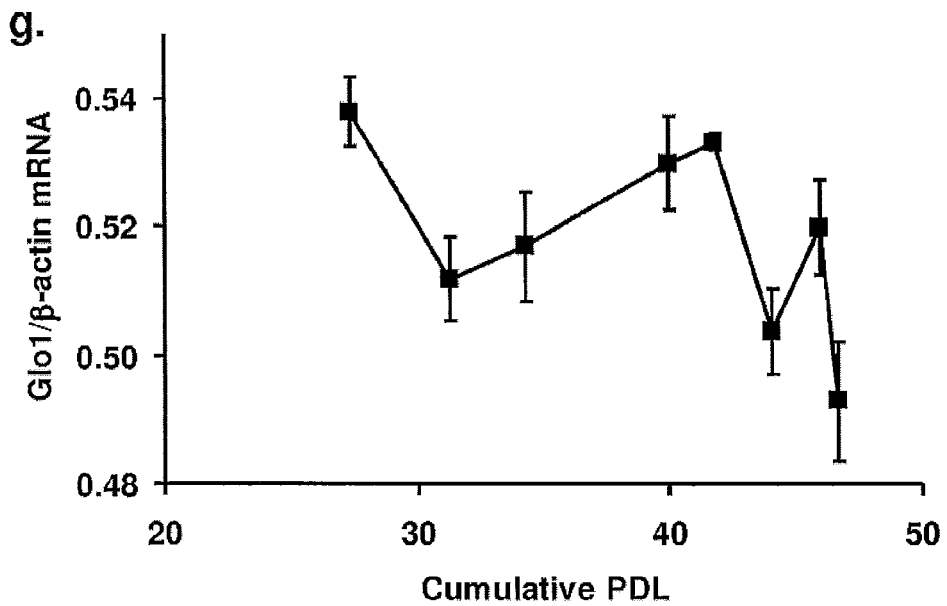

FIG. 3. Shows glyoxalase 1 in the antistress gene response, a. Suppression of endogenous formation of reactive oxygen species (ROS) in HepG2 cells in vitro by 2 μM SFN. b. Suppression of ROS formation induced by 20 μM hydrogen peroxide ($H_2O_2$) in HepG2 cells in vitro by 2 μM SFN. c. Suppression of cytotoxicity induced by 200 $H_2O_2$ in BJ fibroblasts in vitro by 0.5 μM SFN. d. Prevention of frameshift mutations in HepG2 cells in vitro induced by 400 μM MG (400 MG) by 2 μM AITC. e. and f. Suppression of senescence of BJ fibroblasts in vitro. e. Escape from the Hayflick limit by chronic induction of Glo1 expression by 1 μM SFN added once per passage from cumulative population level (PDL) 29.8. f. Delay of the Hayflick limit by induction of Glo1 expression by 0.5 μM SFN added twice, per passage at day 0 and 3 per 7-day passage from cumulative PDL 44.8 Key; O-O, control senescence; ●-●+ SFN. g. Expression of GLO1 in control BJ cells relative to β-actin during the development of senescence. Data are mean±SD (n=3) except in mutation studies where n=3-8.

Figure 4:
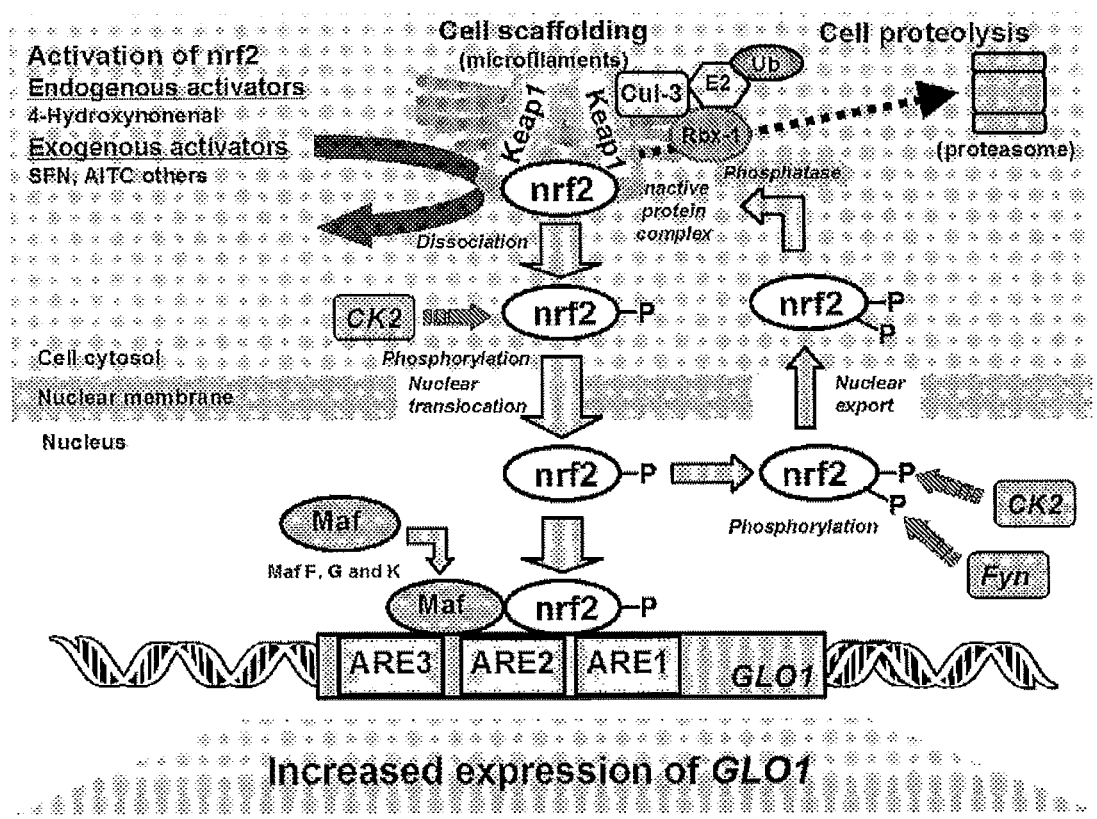

FIG. 4. Shows regulation of nrf2 activation in the antistress gene response and induction of glyoxalase 1 expression. Abbreviations: CK2, casein kinase 2; Cul-3, Cullin-3; E2, ubiquitin activating protein; Fyn, 59-kDa src family-related protein tyrosine kinase; Keap-1, Kelch-like ECH-associated protein 1; Ub, ubiquitin.

Figure 5:
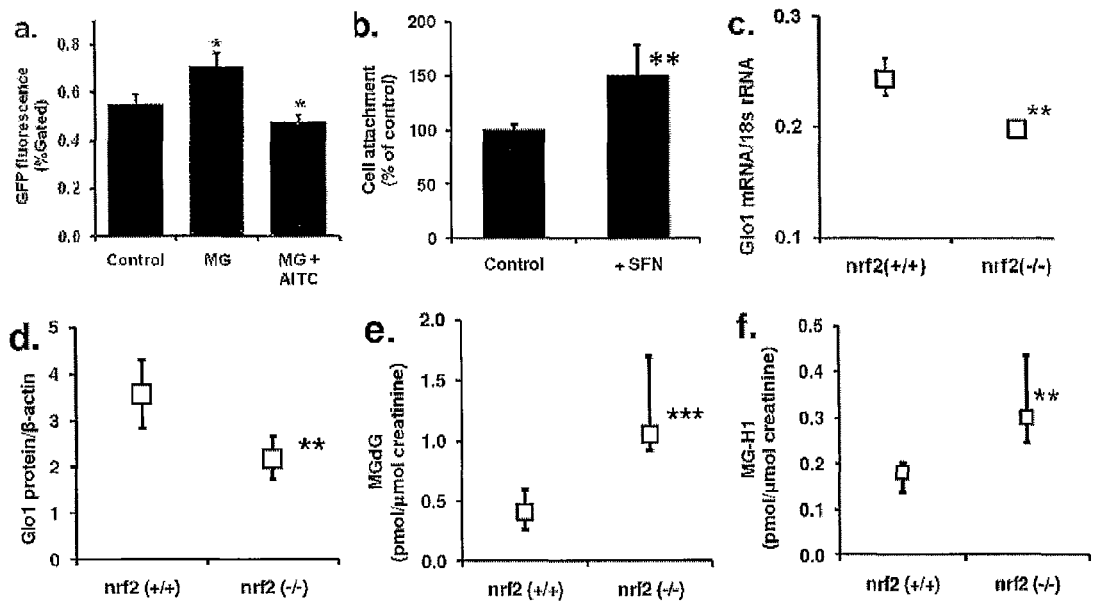
Figure 5:
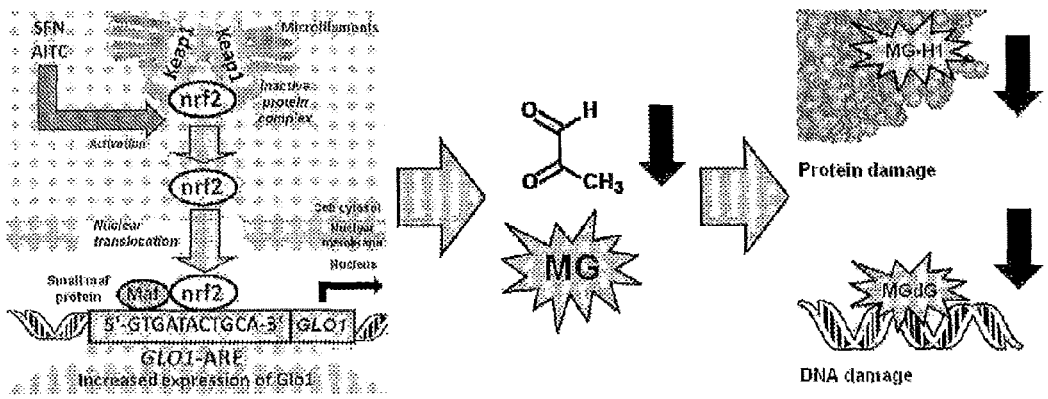

FIG. 5. Shows glyoxalase 1 in the antistress gene response, a. Prevention of frameshift mutations in HepG2 cells in vitro induced by 400 μM MG (400 MG) by 2 μM AITC. b. Improved HMEC-1 endothelial cell adhesion to type IV collagen conditions with medium from BJ cells incubated without (control) and with 2 μM SFN for 24 h. c.-f. Mouse liver Glo1 mRNA, Glo1 protein, and urinary excretion of MGdG and MG-H1 free adducts, respectively, of wild-type nrf2 (+/+) and nrf2 (−/−) mice. Significance: a. and b.—data are mean±SD (n=3); *, P<0.05 and , P<0.01 (t-test), c.-f.—data are median (lower-upper quartile), n=6-9; , P<0.01 and ***, P<0.001 (Mann-Whitney U). g. Conservation of ARE-1 in exon-1 of the GLO1. *Consensus ARE is a weighted consensus ARE derived from comparisons of human, mouse and rat ARE-linked genes.[5] Red entries indicate disparity with human Glo1 ARE of exon-1. h. Schematic summary of transcriptional control of GLO1 by nrf2 for enhanced protection of the proteins and DNA from dicarbonyl glycation damage.

Table 1. Shows GLO1 promoter cloning primers.

Methods

Cell Culture Human hepatoma HepG2 cells and human BJ fibroblasts were cultured in Eagle's Minimum Essential Medium (MEM) medium with 10% foetal calf serum (FCS) and 2 mM glutamine under an atmosphere of 5% $CO_2$ in air, 100% humidity and 37° C. Where sulforaphane was used, the R-stereoisomer was used. R-Sulforaphane (SFN) and allyl isothiocyanate (AITC) were purchased from Sigma-Aldrich (Poole, Dorset, UK).

Frameshift Mutation

The pEGFP-CA/T12 vector is a reporter for efficiency of transfection while pEGFP-CA13 vector is a reporter of frameshift mutation induced by MG.[30] HepG2 cells (2×10[5] cells/well) were cultured in 12-well plates for 24 h, the MEM medium removed, the cells washed with serum free medium and replaced with DNA/lipofectamine complexes in serum free medium—transfection medium (Lipofectamine 2000 reagent, 2 μl; (1.8 μg pEGFP-CA13 or pEGFP-CA/T12; 2.0 ml serum free medium)—and incubated for 5 h at 37° C. The transfection medium was removed and replaced with complete MEM medium supplemented with 10% FCS and 2 mM glutamine) and incubated for 48 h. Transfection efficiency was assessed quantitatively by flow cytometry. HepG2 cells transfected with expression of pEGFP-CA/T12 were incubated with or without 2 μM AITC for 24 h and then with or without 400 μM MG for a further for 48 h. Thereafter, cells were washed with phosphate-buffered saline (PBS) and analysed for GFP expression by flow cytometry.

Real-Time PCR Total RNA was extracted from cultured cells which were treated with SFN, AITC using RNeasy Mini Kit (QIAGEN). cDNAs were synthesized with oligo (dT)18 primer and BioScript reverse transcriptase (BIOLINE). Human GLO1 and ACTB (β-actin reference gene) mRNA were quantified by real-time RT-PCR SYBR green method on ABI 7500 fast real-time PCR system. The following primers were used to amplify GLO1, forward 5'-atgcgacccagagttac-cac-3' (SEQ ID NO: 5) and reverse 5'-ccaggccttttcattttacca-3' (SEQ ID NO: 6). The reference gene ACTB was amplified with primers 5'-ggacttcgagcaagagatgg-3' SEQ ID NO: 7)(forward) and 5'-agcactgtgttggcgtacag-3' (SEQ ID NO: 8)(reverse).

For mouse GLO1, the following primers were used: forward primer sequence 5'-GATCCAGACCCTAGCACCAA-3' (SEQ ID NO: 9) and reverse sequence is 5'-CTTCTGCAG-GAGGGTCAGTC-3' (SEQ ID NO: 10). The reference gene was 18 s rRNA with primers purchased from Qiagen.

Western Blotting Analysis Protein extracts (30 μg) were subjected to SDS-PAGE on 10% polyacrylamide gels. After electrophoresis, the proteins were transferred electrophoretically to PVDF membrane and the membrane blocked with 5% non-fat milk in Tris-buffered saline (TBST; 10 mM Tris-HCl, pH 7.5, 150 mM NaCl, 0.05% Tween-20) and probed with rabbit anti-human Glo1 antibody.[43] The membrane was incubated at 4° C. overnight. After washing, the membrane was incubated with horseradish peroxidase conjugate second antibody for 1 h at room temperature. Immunoreactivity was detected with enhanced chemiluminescence (ECL) and intensities of protein bands were quantified by software ImageQuant TL (GE Healthcare). For reference protein, β-actin, the membrane was stripped with stripping buffer (100 mM β-mercaptoethanol, 2% SDS, 62.5 mM Tris-HCl pH 6.8), blocked with 5% non-fat milk in TBST buffer and re-probed with anti-β-actin antibody with ECL detection.

Construction of Glo1-ARE and Related Reporter Plasmids pGL3-NQO1ARE—Double-stranded DNA oligomer containing the quinone reductase (NQO1) ARE was inserted into pGL3-basic vector by Kpn1 and Nhe1 double digestion to construct an ARE positive reporter vector, pGL3-NQO1ARE. The insertion sequence was (ARE motif is underlined and low case letters are the Kpn1 and Nhe1 restriction sites: ggtaccCTCAGCCTTCCAAATCCCCA GTCA-CAGTGACTCAGCAGAATCgctagc (SEQ ID NO: 4) GLO1 promoter pGL3-basic reporter vector construction—A GLO1 gene fragment extending from −1 (the first base before start codon) to −1176 containing 3 putative AREs and a serial deletion fragments were amplified by PCR from human genomic DNA and cloned into pGL3-basic reporter vector. The primers were used to create deletion mutants of human GLO1 promoter fragments as listed in Table 1. Kpn1 and Nhe1 restriction sites were added in PCR primers 5' and 3' ends. PCR fragments of the 5'-flanking region in GLO1 gene were amplified using human genomic DNA, and cloned into pJET1.2 Cloning Vector with ClonJET™ PCR cloning Kit (Fermentas). The pJET1.2 GLO1 promoter vector was digested with Kpn1 and Nhe1 and the fragments of GLO1 promoter region were sub-cloned into pGL3-basic vector. For the mutant ARE1, the following a mutant anti-sense primer was used to amplify the 5'-flanking region of GLO1 promoter and sub-cloned to pGL3-basic reporter vector. All insertion sequences were confirmed by DNA sequence analysis. Four wild-type and two mutant type pGL3 reporter vectors for GLO1 promoter were constructed.

Transfection and Luciferase Assay of Custom Vectors For luciferase assays, 2×10[5] HepG2 cells per well were plated into 24-well plates and cultured overnight. The cells were transfected with 0.5 μg reporter vector and 10 ng pRL-TK plasmid using Lipofectamine 2000 according to manufacture's protocol. The empty pGL3-basic vector was used as control. After 24 h, 4 μM SFN was added to the cells and vehicle (DMSO) added to control. After 24 h, the cells were washed with PBS and luciferase activity assay performed immediately or samples stored at −80° C. until analysis. For the reporter assay, 100 μl Cell Culture Lysis Reagent (CCLR, Promega) was added to cell extracts and shaken gently for 30 min. The activity mixture was centrifuged (12,000 g, 5 min, 4° C.) and an aliquot (20 μl) of supernatant used in the reporter assay. The luciferase activity was determined using a Dual Luciferase Reporter Assay System (Promega). The relative luciferase activities were normalized by co-transfection of pRL-TK vector.

Cell Adhesion Assays BJ fibroblasts were incubated with and without 2 μM SFN for 24 h. The culture medium was then removed, incubated with human type IV collagen for 24 h and human microvascular endothelial HMEC-1 cell attachment studied as described[13a]. Briefly, BJ cells were incubated with and without 2 μM SFN for 24 h. The medium was then removed and added to wells of a 96-well plate (96-well; Costar; Corning) that had be prior coated type IV collagen. For the coating, 100-□l of 100 □g/ml of type IV collagen (human placental, type IV, pepsin extracted) was added to each well and incubated for 24 h at 37° C. Wells were then washed with phosphate buffered saline. Collagen coated wells were incubated with medium from BK cell cultures for 24 h at 37° C. and then washed with phosphate buffered saline. HMEC-1 endothelial cells (2.5×10[4] cells/well) were plated on to the collagen substrates and incubated for 1 h at 37° C. Non-adherent cells were removed and adherent cells were quantified by staining with 3-(4,5-dimethylthiazole-2-yl)-2,5-diphenyltetrazolium bromide, lysed with dimethylsulfoxide and the blue formazan product detected, by absorbance at 560 nm (Paul, R G, Bailey, A J: The effect of advanced glycation end-product formation upon cell-matrix interactions. Int J Biochem Cell Biol 31: 653-660, 2004).

Other Methods. Activity of Glo1 was determined by measuring the initial rate of isomerisation of the hemithioacetal formed from methylglyoxal and GSH to S-D-lactoylglutathione followed spectrophotometrically at 240 nm.[43] The concentration of MG in cells and culture medium was determined by stable isotopic dilution analysis liquid chromatography with tandem mass spectrometric detection.[4] ROS formation was assessed with dichlorodihydrofluorescein diacetate (H$_2$DCFDA), monitoring the generation of dichlorofluorescein (DCF) fluorescence. HepG2 cells and BJ fibroblasts were incubated with H$_2$DCFDA for 30 min, washed in PBS and DCF fluorescence quantified by flow cytometry.[44]

Animal Studies Experimental procedures were approved by the institutional Animal Experiment Committee of Tohoku University, and experiments were carried out in accordance with the Regulation for Animal Experiments of Tohoku University, Japan or were undertaken in accordance with criteria outlined in a license granted under the Animals (Scientific Procedures) Act 1986, and approved by the Animal Ethics Committees of the University of Liverpool. Generation of the nrf2 knockout mouse and genotyping of progeny have been described elsewhere.[30a] Male mice (from Tohoku University, Sendai, Japan—Prof Masayuki Yamamoto) of approximately 10 weeks of age were used throughout the study. Mice were housed at a temperature range of 19-23° C. under 12-h light/dark cycles and given free access to food and water. Liver samples were snap-frozen immediately in liquid $N_2$, before being stored at −80° C.

Results

Glyoxalase 1 GLO1 is an Antioxidant Response Element-Linked Gene

We assessed whether Glo1 expression might be linked to the antistress gene response coordinated by nuclear factor erythroid 2-related factor 2 (nrf2) binding to one or more antioxidant response elements (AREs) in the Glo1 gene promoter.

The gene for human Glo1, GLO1, is at locus 6p21.3-p21.1. Previous analysis of the 5'-flanking region revealed the presence of a functional insulin response element and metal response element.[22] Our inspection of this region revealed the presence of antioxidant response elements located at (numbered from the start codon): −10 to −19, sequence 5'-GTl-GATACTGCA-3' (SEQ ID NO: 1)in exon-1 (ARE1): −261 to −252, sequence 5'-ATGAGTTTGCC-3' (SEQ ID NO: 2)(ARE2); and −1060 to −1051, sequence 5'-ATGAC-TAAGCC-3' (SEQ ID NO: 3)(ARE3). Construction of luciferase reporter vectors with whole or segments of this promoter-exon-1 untranslated region showed that a combination of ARE1 and ARE2 gave maximal induction of Glo1 transcriptional response and a combination of all 3 AREs provided a transcriptional response slightly decreased from the maximal response—FIG. 1d. Mutation of the AREs blocked the transcriptional response—FIG. 1e. This indicates that there are functional AREs in the GLO1 and that GLO1 is potentially a gene with expression inducible by activators of nrf2 in the antistress gene response. Further, construction of luciferase reporter vectors with whole or segments of this region and activation with the nrf2 activator sulforaphane (SFN) showed that ARE1 alone gave maximal induction of Glo1 transcriptional response and ARE-2 and ARE-3 had little further effect on the inducible transcriptional response—FIG. 1d. Mutation of the ARE-1 blocked the transcriptional response—FIG. 1e, indicating that GLO1 is a gene with expression inducible by activators of nrf2.

Glyoxalase 1 in the Antistress Gene Response

The antistress gene response coordinates induction of protective gene expression and repression of lipogenic gene expression for survival and defense in stressful conditions. Potent activators are dietary isothiocyanates such as sulforaphane (SFN) and allyl isothiocyanate (AITC).[25] Responses of Glo1 expression were studied in human hepatoma HepG2 cells and human BJ fibroblasts in vitro. With treatment by nrf2 activators, 2 μM SFN and 2 μM AITC, the activity of Glo1 was increased 2-3 fold—FIG. 2, a. and b. There was a related dose-dependent increase in Glo1 mRNA which in time course increased from 4 h, maximised at 12 h post-treatment with the inducer and declined back to baseline levels thereafter—FIG. 2 c. and d. Assessment of the gene product showed an increase in Glo1 protein progressively over 16 h following the increase in Glo1 mRNA. At 24 h post-treatment there was still a marked decrease in the concentration of methylglyoxal in the cell culture. This shows that nrf2 inducers increase Glo1 expression and activity producing the desired metabolic response of decrease in methylglyoxal concentration. Some compounds known to be activators of nrf2, however, are not potent inducers of Glo1 expression—such as tert-butylhydroquinone, indole-3-carbinol and diallyldisulphide—data not shown. This may be due to failure to recruit the appropriate accessory proteins—small maf protein and others, or by premature activation of regulatory kinases which switch off nrf2 induced gene expression by activating nuclear export of nrf2.

Silencing of nrf2 expression with siRNA decreased the basal mRNA of Glo1 and blocked the increase of Glo1 mRNA in response to SFN—FIG. 2g. At 24 h post-treatment there was decreased concentration of MG in the cell culture medium and cells—FIG. 2, h. and i., and related decrease in cellular protein MG-H1 residue content developed after 48 h—FIG. 2, j.

Activation of nrf2, therefore, increased Glo1 expression and activity, decreasing cellular and extracellular concentrations of MG leading to decreased damage to cellular protein. Functional Effects Linked to Induction of Glyoxalase 1 by the Antistress Gene Response We have previously shown that modification of mitochondrial proteins by MG in ageing is critical to increased formation of reactive oxygen species (ROS; superoxide, hydrogen peroxide and hydroxyl radical) and overexpression of Glo1 protects against this.[20] Induction of Glo1 activity by SFN in HepG2 cells in vitro was associated with decrease in endogenous ROS (FIG. 3a) and increased ROS induced, by exogenous hydrogen peroxide (20 μM)—FIG. 3b. Increased concentrations of exogenous hydrogen peroxide induced cytotoxicity in vitro where scavenging of MG with aminoguanidine was protective.[28] For BJ fibroblasts, incubation with 200 μM hydrogen peroxide decreased cell viability to 74%. Prior but not concurrent incubation with 0.5 μM SFN for 24 h increased viability during exposure 200 μM hydrogen peroxide to 88%—FIG. 3c.

To assess effect of induction of GLO1 expression in mutagenesis a frameshift mutation-dependent green fluorescent protein (GFP) reporter expression vector and GFP-constitutive expression vector control were used.[29,30] HepG2 cells have relatively high constitutive expression of GLO1 and are resistant to toxicity of MG; the median growth inhibitory concentration of MG was 1.07±0.08 mM (n=8). Exposure of HepG2 cells to 400 μM MG increased frameshift mutation-dependent GFP which was prevented by induction of GLO1 expression by prior exposure to 2 μM AITC—FIG. 3d.

Normal ageing may be modelled in human cells in vitro by cell senescence. Hunan dermal BJ fibroblasts are an established model of cell senescence where by 49 population doublings (cumulative population doubling level PDL=49) cell growth stops as the Hayflick limit is reached—FIG. 3, e. and f. GLO1 expression undergoes decline and recovery from cumulative PDL 27-46 and then enters terminal decline immediately prior to senescence—FIG. 3g. Induction of GLO1 expression by treatment of BJ cells with 1.0 μM SFN per passage, initiating dosing at cumulative PDL 30, allowed escape from the Hayflick limit—FIG. 3e. BJ fibroblasts treated with 1.0 μM SFN in this way maintained an increase in cell number >3-fold per passage beyond cumulative PDL 53 and grew indefinitely until destroyed deliberately with a biocidal agent. With a lower dose (2×0.5 μM SFN per passage) and initiated closer to senescence (at cumulative PDL 45) produced a weaker response but nevertheless delayed senescence of BJ cells—the Hayflick limit being delayed to cumulative PDL=50.5—FIG. 3f.

To study the functional effects of Glo1 induction in the antistress gene response, we assessed the effect on MG-induced mutagenesis. HepG2 cells have relatively high basal expression of Glo1 and are resistant to toxicity and mutagenesis induced by MG; the median growth inhibitory concentration of MG was 1.07±0.08 mM (n=8). Using a fluorogenic frameshift mutation reporter[22a] we found that exposure of HepG2 cells to 400 mM MG increased frameshift mutations. This was prevented by prior induction of Glo expression by 2 µM AITC—FIG. 5a. Increased release of MG from cells increases modification of arginine residues in integrin binding sites of extracellular matrix proteins and decreases cell-extracellular matrix interactions leading to cell detachment and anoikis.[13a,23] Induction of Glo1 expression in BJ fibroblasts decreased extracellular MG—see above. Conditioning of type IV collagen in this MG-depleted medium preserved the binding of endothelial cells beyond that found with control culture medium—FIG. 5b.

To assess if MG modification of DNA and protein was related to nrf2 transcriptional control in vivo, we measured the urinary efflux of nucleoside adduct MGdG and arginine-derived MG-H1 free adduct in wild-type and mutant nrf2 (−/−) mice. There was decreased expression of Glo1 in mutant nrf2 (−/−) mice, as evidenced by decreased Glo1 mRNA and protein in the liver—FIG. 5 c. and d. There was a ca.2-fold increase in urinary excretions of MGdG and MG-H1 in nrf2 (−/−) mice with respect to wild type nrf2 (+/+) controls, suggesting that the nrf2 system does indeed serve to protect against MG-mediated nucleotide and protein damage in vivo—FIG. 5, e and f.

Investigation of species conservation of ARE1 in the GLO1 gene showed high sequence identity in primates and high sequence identity and similarity in mouse, rat, pig and cow, and with the overall consensus human ARE motif for basal and inducible expression[5]—FIG. 5g.

Discussion

Modification of proteins and DNA by MG and related reactive dicarbonyl substrates of Glo1 is one of the most important threats to the functional integrity of the proteome and genome. Ageing, metabolic stress and inflammation are linked to increase concentrations of MG in tissues and body fluids. Enhanced protection against dicarbonyl damage by induction of Glo1 expression via activation of the antistress gene response is a mechanism by which the nrf2 system can act as a guardian of physiological systems.

A clinically effective Glo1 inducer is likely to find therapeutic application in microvascular and macrovascular complications of diabetes, non-diabetic vascular disease—particularly in renal failure, neuropathic pain, certain neurological disorders (pathologic anxiety, Alzheimer's disease, Parkinson's disease and others), other chronic diseases and ageing.

REFERENCES

5. Wang, X. et al. Identification of polymorphic antioxidant response elements in the human genome. Hum. Mol. Genet. 16, 1188-1200 (2007).
13. Yao, D, et al. High glucose increases angiopoietin-2 transcription in microvascular endothelial cells through methylglyoxal modification of mSin3A. Journal of Biological Chemistry 282, 31038-31045 (2007).
13a. Dobler, D. et al. Increased dicarbonyl metabolism in endothelial cells in hyperglycemia induces anoikis and impairs angiogenesis by ROD and GFOGER motif modification. Diabetes 55, 1961-1969 (2006).
14. Ceradini, D. J. et al. Decreasing Intracellular Superoxide Corrects Defective Ischemia-induced New Vessel Formation in Diabetic Mice. Journal of Biological Chemistry 283, 10930-10938 (2008).
15. Yao, D. C. & Brownlee, M. Hyperglycemia-Induced Reactive Oxygen Species Increase Expression of the Receptor for Advanced Glycation End Products (RAGE) and RAGE Ligands. Diabetes 59, 249-255 (2010).
16. Queisser, M. A. et al. Hyperglycemia Impairs Proteasome Function by Methylglyoxal. Diabetes 59, 670-678 (2010).
17. Ahmed, U., Dobler, D., Larkin, S. J., Rabbani. N. & Thornalley. P. J. Reversal of hyperglycemia-induced angiogenesis deficit of human endothelial cells by overexpression of glyoxalase I in vitro. Maillard Reaction: Recent Advances in Food and Biomedical Sciences 1126, 262-264 (2008).
18. Brouwers. O. et al. Hyperglycaemia-induced impairment of endothelium-dependent vasorelaxation in rat mesenteric arteries is mediated by intracellular methylglyoxal levels in a pathway dependent on oxidative stress. Diabetologia.
19. Kumagai, T. et al. Glyoxalase I overexpression ameliorates renal ischemia-reperfusion injury in rats. Am J Physiol Renal Physiol 296, F912-F921 (2009).
20. Morcos, M. et al. Glyoxalase-1 prevents mitochondrial protein modification and enhances lifespan in *Caenorhabditis elegans*. Aging Cell 7, 260-269 (2008).
21. Wasserman, W. W. & Fahl, W. E. Functional antioxidant responsive elements. Proceedings of the National Academy of Sciences of the United States of America 94, 5361-5366 (1997).
22. Ranganathan, S., Ciaccio, P. J., Walsh, E. S. & Tew, K. D. Genomic sequence of human glyoxalase-I: analysis of promoter activity and its regulation. Gene 240, 149-155 (1999).
22a. Gasche, C. et al. Oxidative Stress Increases Frameshift Mutations in Human Colorectal Cancer Cells. Cancer Research 61, 7444-7448 (12001).
23. Duran-Jimenez. B. et al. Advanced Glycation Endproducts in extracellular matrix proteins contribute to the failure of sensory nerve regeneration in diabetes. Diabetes 58, 2893-2903 (2009).
25 Jeong, W. S. et al. Differential expression and stability of endogenous nuclear factor E2-related factor 2 (Nrf2) by natural chemopreventive compounds in HepG2 human hepatoma cells. Journal of Biochemistry and Molecular Biology 38, 167-176 (2005).
28. Abordo, E. A., Minhas, H. S. & Thornalley, P. J. Accumulation of a-oxoaldehydes during oxidative stress. A role in cytotoxicity. Biochem. Pharmacol. 58, 641-648 (1999).
29. Hausner, P., Venzon, D. J., Grogan, L. & Kirsch, I. R. The "comparative growth assay": Examining the interplay of anti-cancer agents with cells carrying single gene alterations. Neoplasia (New York) 1, 356-367 (1999).
30. Gasche, C., Chang, C. L., Rhees, J., Goel, A. & Boland, C. R. Oxidative Stress Increases Frameshift Mutations in Human Colorectal Cancer Cells. Cancer Research 61, 7444-7448 (2001).
30a. Itoh, K. et al. An Nrf2/Small Maf Heterodimer Mediates the Induction of Phase II Detoxifying Enzyme Genes through Antioxidant Response Elements. Biochemical and Biophysical Research Communications 236, 313-322 (1997).
33. Barati, M. T. et al. Proteomic analysis defines altered cellular redox pathways and advanced glycation end-prod- 34. Staniszewska, M. & Nagaraj, R. Upregulation of Glyoxalase I fails to Normalize Methylglyoxal Levels: A Possible Mechanism for Biochemical. Changes in Diabetic Mouse Lenses. Molecular and Cellular Biochemistry 288, 29-36 (2006).
35. Tafti, M. at al. Deficiency in short-chain fatty acid b-oxidation affects theta oscillations during sleep. Nat Genet 34, 320-325 (2003).
36. Stoyanov, S. B. et al. Loss of glyoxalase-1 promotes hyperalgesia in early diabetic neuropathy. Diabetologia 52, 1146 (2009).
37. Chen, X. L., Dodd, G. & Kunsch, C. Sulforaphane inhibits TNF-alpha-induced activation of p38 MAP kinase and VCAM-1 and MCP-1 expression in endothelial cells. Inflammation Research 58, 513-521 (2009).
41. Ahmed, N. et al. Protein glycation, oxidation and nitration marker residues and free adducts of cerebrospinal fluid in Alzheimer's disease and link to cognitive impairment. J. Neurochem. 92, 255-263 (2004).
43. Allen, R. E., Lo, T. W. C. & Thornalley, P. J. A simplified method for the purification of human red blood cell glyoxalase 1. Characteristics, immunoblotting and inhibitor studies. J. Prot. Chem. 12, 111-119 (1993).
44. Xue, M. et al. Activation of NF-E2-Related Factor-2 Reverses Biochemical Dysfunction of Endothelial Cells Induced by Hyperglycemia Linked to Vascular Disease. Diabetes 57, 2809-2817 (2008).
45. Konrade, I, Stoyanov, S, Haag, G M, Seregin, Y, Humpert, P M, Morcos, M, Thorpe, S R, Thornalley, P, Nawroth, P P, Bierhaus, A: RAGE-dependent impairment of glyoxalase-1 contributes to functional deficits in diabetic neuropathy. Diabetologia 49: 662, 2006.
46. Ahmed N. Ahmed U, Thornalley P J, Watts R, Tarr J, Haigh R, Winyard P: Profound increase in proteolytic products of glycated and oxidised proteins in synovial fluid and plasma in osteoarthritis and rheumatoid arthritis, corrected by tnf-á antibody therapy in rheumatoid arthritis (Abstract). Rheumatology 45, Suppl. 1, 2006.
47. Thornalley, P J: The potential role of thiamine (vitamin B1) in diabetic complications. Curr. Diabetes Res. 1:287-298, 2005.
48. Rabbani & Thornalley: Glyoxalase in diabetes, obesity and related disorders. Seminars in Cell and Development Biology 22:309-317, 2011.
49. Xue M et al: Glycoxylase in Ageing Seminars in Cell and Development Biology 22: 293-301, 2011.
50. Rabbani et al: Glycation of LDL by Methylglyoxal Increases Arterial Atherogenicity A Possible Contributor to Increased Risk of Cardiovascular Disease in Diabetes 1:1-8, 2011.

TABLE 1

GL01 promoter cloning primers

| Deletion mutant | Forward | Reverse | ARE-like sequence including: | Size of fragment |
|---|---|---|---|---|
| F1 | Ttggtacctgcccaacctcattttggtta (SEQ ID NO: 11) | Ttgctagctggctgaactgcagtatcaca (SEQ ID NO: 12) | ARE(1,2,3) | 1176 |
| F2 | Ttggtacctcacttcagcccaggagt (SEQ ID NO: 13) | Ttgctagctggctgaactgcagtatcaca (SEQ ID NO: 12) | ARE(1,2) | 850 |
| F3 | Ttggtacctgcctcctttatgcgcaag (SEQ ID NO: 14) | Ttgctagctggctgaactgcagtatcaca (SEQ ID NO: 12) | ARE(1) | 256 |
| F1 | Ttggtacctgcccaacctcattttggtta (SEQ ID NO: 11) | Ttgctagcactgaccctctctgagcttcc (SEQ ID NO: 15) | ARE3 | 622 |
| ARE1 mutant |  | Ttgctagctggctgaactgcagtatcaca (SEQ ID NO: 12) | ARE(1,2,3)m |  |
| F1 | Ttggtacctgcccaacctcattttggtta (SEQ ID NO: 11) | TtgctagctggctgaactgcagtTATCcagacga (SEQ ID NO: 17) | (ARE1,2)m | 1176 |
| F3 | Ttggtacctgcctcctttatgcgcaag (SEQ ID NO: 14) | TtgctagctggctgaactgcagtTATCcagacga (SEQ ID NO: 17) | ARE(1)m | 256 |

Note:
Upper case letters are mutant bases. The sequences for Kpn1 and Nhe1 restriction sites are underlined.

The invention claimed is:

1. A screening method for identifying agents that prevent and/or reverse proteomic and/or genomic damage, by dicarbonyl substrates of Glo1, by inducing the increased expression of the GLO1 gene comprising:
   a) providing a cell including the GLO1 gene promoter functionally coupled to the coding region of the GLO1 gene and/or the coding region of a selected reporter gene and associated transcription machinery for producing a Glo1 gene product and/or a reporter gene product;
   b) exposing said cell to at least one test agent;
   c) investigating said cell for the production of said GLO1 gene product and/or reporter gene product; and
   d) where said product is produced, or its amount increased, after exposure to the test agent, concluding said test agent has use in inducing the expression of Glo1 and so preventing proteomic and genomic damage by dicarbonyl substrates of Glo1.

2. The method according to claim 1 wherein said cell is a recombinant cell that has been transformed or transfected with a construct encoding said GLO1 gene.

3. The method according to claim 1 wherein said GLO1 gene comprises at least one antioxidant response element (ARE).

4. The method according to claim 1 wherein said GLO1 gene comprises a plurality of AREs.

5. The method according to claim 3 or claim 4 wherein said ARE is selected from the group consisting of:

```
         (ARE1)
                                       (SEQ ID NO: 1)
         5'-GTGATACTGCA-3', (ARE2)
                                       (SEQ ID NO: 2)
         5'-ATGAGTTTGCC-3',
         and (ARE3)
                                       (SEQ ID NO: 3)
         5'-ATGACTAAGCC-3'.
```

6. The method according to claim 4 wherein at least the following pair of AREs is present:

```
         ARE1 and ARE2 i.e. sequences
                                       (SEQ ID NO: 1)
         5'-GTGATACTGCA-3'
         and
                                       (SEQ ID NO: 2)
         5'-ATGAGTTTGCC-3'.
```

7. The method according to claim 1 wherein said GLO1 gene comprises the wild-type promoter.

8. The method according to claims 1 wherein said GLO1 gene comprises an artificial promoter.

9. The method according to claim 1 wherein said cell comprises the following construct:

```
                                                 (SEQ ID NO: 4)
GgtaccCTCAGCCTTCCAAATCCGCAGTCACAGTGACTCAGCAGAATCg
ctagc
```

10. A construct encoding the promoter region of the GLO1 gene or a recombinant version thereof, functionally linked to a coding region of a gene encoding a reporter molecule, wherein said construct comprises GLO1 ARE1.

11. The construct according to claim 10 wherein said reporter molecule is a fluorescent molecule.

12. A cell or cell line transformed or transfected with a construct according to claim 10.

13. A kit for identifying agents that prevent proteomic and/or genomic damage by dicarbonyl substrates of GLO1 by inducing the increased expression of the GLO1 gene comprising:
   a) a cell or construct including the GLO1 gene promoter, or a recombinant version thereof, including an artificial promoter comprising a plurality of AREs, functionally coupled to the coding region of the GLO1 gene and/or the coding region of a selected reporter gene and associated transcription machinery for producing a GLO1 gene product or a reporter gene product; and
   b) an assay means for measuring the presence or amount of GLO1 product or the presence or amount of reporter molecule, and/or for measuring the activity of GLO1.

14. A screening method for identifying agents that prevent proteomic and genomic damage by dicarbonyl substrates of GLO1 by inducing the increased activity of GLO1 protein comprising:

a) providing a cell or media including the GLO1 protein;
b) exposing said protein to at least one test agent;
c) investigating said protein to determine its activity; and
d) where said activity is increased following exposure to said test agent, concluding said test agent has use in increasing the activity of GLO1 protein and so preventing proteomic and genomic damage by dicarbonyl substrates of GLO1.

15. A construct encoding an artificial promoter comprising GLO1 ARE1.

16. The construct according to claim 15 further comprising an encoding region of a GLO1 gene and/or a coding region of a gene encoding a reporter molecule functionally linked to said promoter.

17. The construct according to claim 16 wherein said reporter molecule is a fluorescent molecule.

18. A cell or cell line transformed or transfected with the construct according to claim 15.

19. A method for the identification of agents that induce the expression of a gene functionally coupled to either the wild-type GLO1 promoter or a recombinant version thereof including an artificial promoter comprising a plurality of AREs, comprising exposing a cell or cell line according to claim 18 to the agents.

20. The method according to claim 19 where said gene is GLO1 or a selected reporter gene.

21. A method for the identification of agents that induce the expression of a gene functionally coupled to either the wild-type GLO1 promoter or a recombinant version thereof including an artificial promoter comprising a plurality of AREs, comprising exposing a cell or cell line according to claim 12 to the agents.

22. The method according to claim 21 wherein said gene is GLO1 or a selected reporter gene.

* * * * *

SEQUENCE LISTING

<160> NUMBER OF SEQ ID NOS: 27

<210> SEQ ID NO 1
<211> LENGTH: 11
<212> TYPE: DNA
<213> ORGANISM: Homo sapien

<400> SEQUENCE: 1
gtgatactgc a    11

```
<210> SEQ ID NO 2
<211> LENGTH: 11
<212> TYPE: DNA
<213> ORGANISM: Homo sapien

<400> SEQUENCE: 2
atgagtttgc c                                                            11

<210> SEQ ID NO 3
<211> LENGTH: 11
<212> TYPE: DNA
<213> ORGANISM: Homo sapien

<400> SEQUENCE: 3
atgactaagc c                                                            11

<210> SEQ ID NO 4
<211> LENGTH: 54
<212> TYPE: DNA
<213> ORGANISM: Homo sapien

<400> SEQUENCE: 4
ggtaccctca gccttccaaa tccgcagtca cagtgactca gcagaatcgc tagc             54

<210> SEQ ID NO 5
<211> LENGTH: 20
<212> TYPE: DNA
<213> ORGANISM: Homo sapien

<400> SEQUENCE: 5
atgcgaccca gagttaccac                                                   20

<210> SEQ ID NO 6
<211> LENGTH: 20
<212> TYPE: DNA
<213> ORGANISM: Homo sapien

<400> SEQUENCE: 6
ccaggccttt cattttacca                                                   20

<210> SEQ ID NO 7
<211> LENGTH: 20
<212> TYPE: DNA
<213> ORGANISM: Homo sapien

<400> SEQUENCE: 7
ggacttcgag caagagatgg                                                   20

<210> SEQ ID NO 8
<211> LENGTH: 20
<212> TYPE: DNA
<213> ORGANISM: Homo sapien

<400> SEQUENCE: 8
agcactgtgt tggcgtacag                                                   20

<210> SEQ ID NO 9
<211> LENGTH: 20
<212> TYPE: DNA
<213> ORGANISM: Mus musculus

<400> SEQUENCE: 9
gatccagacc ctagcaccaa                                                   20
```

<210> SEQ ID NO 10
<211> LENGTH: 20
<212> TYPE: DNA
<213> ORGANISM: Mus musculus

<400> SEQUENCE: 10
cttctgcagg agggtcagtc                                              20

<210> SEQ ID NO 11
<211> LENGTH: 29
<212> TYPE: DNA
<213> ORGANISM: Homo sapien

<400> SEQUENCE: 11
ttggtacctg cccaacctca ttttggtta                                    29

<210> SEQ ID NO 12
<211> LENGTH: 29
<212> TYPE: DNA
<213> ORGANISM: Homo sapien

<400> SEQUENCE: 12
ttgctagctg gctgaactgc agtatcaca                                    29

<210> SEQ ID NO 13
<211> LENGTH: 26
<212> TYPE: DNA
<213> ORGANISM: Homo sapien

<400> SEQUENCE: 13
ttggtacctc acttcagccc aggagt                                       26

<210> SEQ ID NO 14
<211> LENGTH: 27
<212> TYPE: DNA
<213> ORGANISM: Homo sapien

<400> SEQUENCE: 14
ttggtacctg cctcctttat gcgcaag                                      27

<210> SEQ ID NO 15
<211> LENGTH: 29
<212> TYPE: DNA
<213> ORGANISM: Homo sapien

<400> SEQUENCE: 15
ttgctagcac tgaccctctc tgagcttcc                                    29

<210> SEQ ID NO 16
<211> LENGTH: 34
<212> TYPE: DNA
<213> ORGANISM: Homo sapien

<400> SEQUENCE: 16
ttgctagctg gctgaactgc agttatccag acga                              34

<210> SEQ ID NO 17
<211> LENGTH: 34
<212> TYPE: DNA
<213> ORGANISM: Homo sapien

<400> SEQUENCE: 17

```
ttgctagctg gctgaactgc agttatccag acga                                  34
```

```
<210> SEQ ID NO 18
<211> LENGTH: 11
<212> TYPE: DNA
<213> ORGANISM: mammalian

<400> SEQUENCE: 18
gtgactcagc a                                                           11

<210> SEQ ID NO 19
<211> LENGTH: 11
<212> TYPE: DNA
<213> ORGANISM: Pan troglodytes

<400> SEQUENCE: 19
gtgatactgc a                                                           11

<210> SEQ ID NO 20
<211> LENGTH: 11
<212> TYPE: DNA
<213> ORGANISM: Gorilla gorilla

<400> SEQUENCE: 20
gtgatactgc a                                                           11

<210> SEQ ID NO 21
<211> LENGTH: 11
<212> TYPE: DNA
<213> ORGANISM: Macaca sp.

<400> SEQUENCE: 21
gtgatactgc a                                                           11

<210> SEQ ID NO 22
<211> LENGTH: 11
<212> TYPE: DNA
<213> ORGANISM: Callithrix jacchus

<400> SEQUENCE: 22
gtgatactgc a                                                           11

<210> SEQ ID NO 23
<211> LENGTH: 11
<212> TYPE: DNA
<213> ORGANISM: Mus musculus

<400> SEQUENCE: 23
gtgattctcc a                                                           11

<210> SEQ ID NO 24
<211> LENGTH: 11
<212> TYPE: DNA
<213> ORGANISM: Rattus sp.

<400> SEQUENCE: 24
gcgattctcc a                                                           11

<210> SEQ ID NO 25
<211> LENGTH: 3
<212> TYPE: DNA
<213> ORGANISM: Oryctolagus cuniculus

<400> SEQUENCE: 25
```

```
gct                                                           3

<210> SEQ ID NO 26
<211> LENGTH: 11
<212> TYPE: DNA
<213> ORGANISM: Bos sp.

<400> SEQUENCE: 26
gtgatacagc a                                                  11

<210> SEQ ID NO 27
<211> LENGTH: 10
<212> TYPE: DNA
<213> ORGANISM: Sus sp.

<400> SEQUENCE: 27
gtgatacgca                                                    10
```